(12) United States Patent
McLaughlin et al.

(10) Patent No.: US 6,983,662 B2
(45) Date of Patent: Jan. 10, 2006

(54) BODILY FLOW MEASURING SYSTEM

(75) Inventors: James McLaughlin, Belfast (GB); Paul Irwin, Cookstown (GB)

(73) Assignee: Uutech Limited, Coleraine (GB)

( * ) Notice: Subject to any disclaimer, the term of this patent is extended or adjusted under 35 U.S.C. 154(b) by 0 days.

(21) Appl. No.: 10/257,587

(22) PCT Filed: Apr. 11, 2001

(86) PCT No.: PCT/GB01/01625

§ 371 (c)(1),
(2), (4) Date: Mar. 5, 2003

(87) PCT Pub. No.: WO01/76473

PCT Pub. Date: Oct. 18, 2001

(65) Prior Publication Data

US 2003/0163055 A1    Aug. 28, 2003

(51) Int. Cl.
*G01F 1/34* (2006.01)
(52) U.S. Cl. .................................. 73/861.42
(58) Field of Classification Search ..............
73/861.42–861.45, 861.46; 600/490, 493
See application file for complete search history.

(56) References Cited

U.S. PATENT DOCUMENTS

| | | |
|---|---|---|
| 3,517,661 A | 6/1970 | Buffington |
| 4,771,792 A * | 9/1988 | Seale .......................... 600/587 |
| 5,807,278 A * | 9/1998 | McRae ........................ 600/579 |
| 6,200,270 B1 * | 3/2001 | Biehl et al. .................. 600/493 |
| 6,346,083 B1 * | 2/2002 | Nishibayashi et al. ...... 600/490 |

FOREIGN PATENT DOCUMENTS

| | | |
|---|---|---|
| DE | 19609698 A | 9/1997 |
| EP | 0386619 A | 9/1990 |
| EP | 0824009 A | 2/1998 |
| GB | 2211616 A | 7/1989 |
| WO | WO 0010453 A | 3/2000 |

* cited by examiner

*Primary Examiner*—Harshad Patel
*Assistant Examiner*—Corey D. Mack
(74) *Attorney, Agent, or Firm*—Kirkpatrick & Lockhart Nicholson Graham LLP

(57) ABSTRACT

A system of measuring the flow of a human or animal bodily action or fluid along or through a bodily flow conduit using two or more sensor means located on the body and along or around the path of the conduit is described. Bodily fluids whose flow is measurable by the present invention include blood, semen and urine. The present invention is a non-invasive way of measuring the flow of a bodily action or fluid along or through a conduit, such as pulse wave velocity. Pulse wave velocity in the brachial artery can provide an indication of vessel wall quality or stiffness, which in turn, can be used to indicate how an individual's vascular system is ageing. Disorders such as stenosis and complete occlusion can be diagnosed by accurate measurement of pulse wave velocity.

31 Claims, 9 Drawing Sheets

*Fig. 4b*
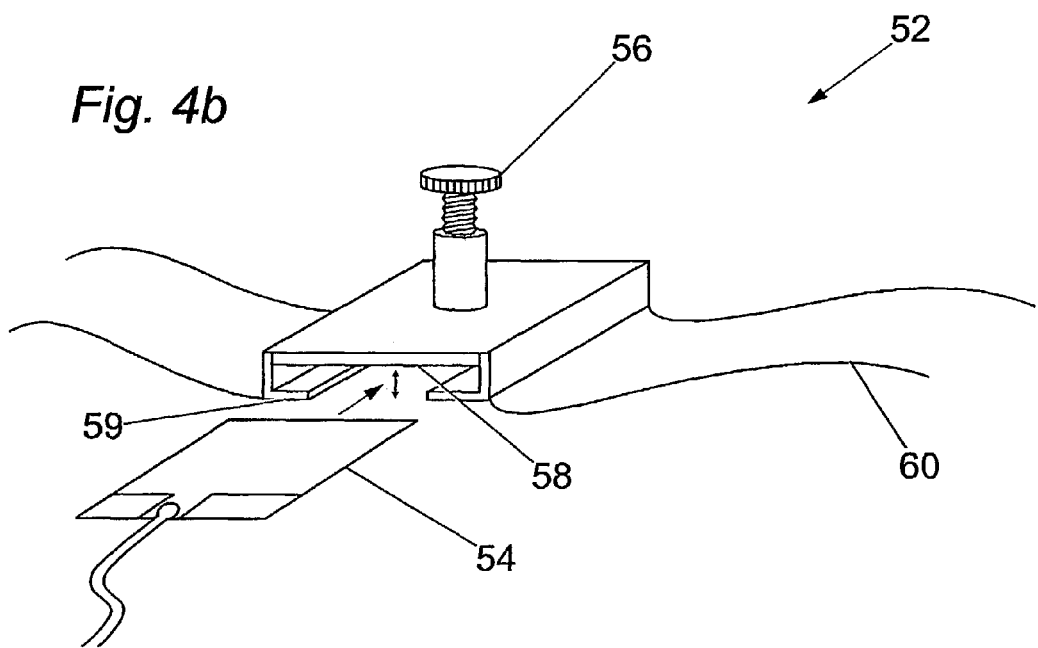
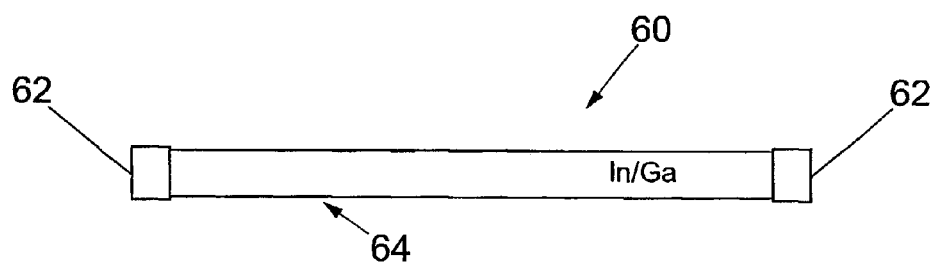
*Fig. 4c*

BODILY FLOW MEASURING SYSTEM

The present invention relates to a system and method for measuring the flow of bodily fluids such as blood or semen, or action such as pulse wave velocity, and apparatus and means therefor.

Current research suggests that 850 people with hypertension have to be treated for 1 year to prevent 1 stroke. Anything that would allow a general practitioner in the primary health care setting to be more specific in preventing vascular disease would be of benefit.

A review of the literature suggests that pulse wave velocity (PWV) could be used as a means of indirectly assessing vessel wall stiffness. Vessel wall stiffness has been found to be an indicator of sub-clinical atherosclerosis in clinical hypertension, and that the presence of sub-clinical atherosclerosis predicts an increased risk of overt vascular disease. Evaluation of the arterial wall elasticity is a possible way of diagnosing the onset of vascular impairment at an early stage and could facilitate the effective treatment of this problem.

Pulse wave velocity measurement is well established in physiological research and has been useful in measuring the effects of diabetes and hypertension on blood vessels. Some modern cardiovascular drugs have been shown to influence PWV and it may be that, in the future, adjustment of PWV by therapeutic means could reduce the incidence of vascular disease.

Following each cardiac contraction, a pressure wave is generated in the aorta. The radial stress applied to a arterial wall creates a local deformation which propagates from the heart to peripheral sites. As PWV depends on the elastic properties of the arterial wall, it is widely used as an index in healthy subjects or in patients suffering form various diseases. A high wall stiffness is a condition which persists at all times of the day regardless of activity or mental state. The sufferer may not feel ill but may still be at risk of developing heart disease and/or a disturbance of the circulation. The longer this condition goes undetected the greater the risk that one of the aforementioned diseases could result in death.

Currently there is research into pulse wave velocity measuring systems and into the development of devices utilising a range of techniques including: Doppler ultrasound techniques; fibre optic measurement systems and electrical impedance measurements. However, the devices presently being used have disadvantages including their high error margin. Ultra-sonic methods can only be done in hospital, and the measurements have aberrations caused by the distortion of the waves as they pass through body tissue.

There is need therefore for a low cost, non-invasive method to measure PWV.

According to one aspect of the present invention, there is provided a system of measuring the flow of a human or animal bodily action or fluid along or through a bodily flow conduit using two or more sensor means located on the body along or around the path of the conduit.

The present invention equally provides a method for making such measurements.

Bodily actions include pulse waves. Thus, in one embodiment of the present invention, there is provided a pulse wave velocity measuring system comprising two or more pressure sensor means, preferably arranged along a support means, such that at least two of the sensor means are locatable over a bodily fluid conduit such as an artery of a human or animal body, and a means to transfer signals from the sensor means to a signal processing means adapted to calculate the pulse wave velocity between the sensors.

Bodily fluids whose flow is measurable by the present invention include blood, semen and urine. Blood flow through a major artery or areas such as the carotids, aorta and distal arteries e.g. in the legs, is measurable. The speed or velocity of seminal fluid during ejaculation is also measurable.

In all circumstances of bodily actions or fluids passing along or through a conduit, there is an electrical and/or mechanical indicator or signal, such as an electrical or muscular discharge, differential or deformation. It is such signals that can be detected by sensor means.

The electrical or mechanical signal may be directly associated with the conduit, e.g. a pressure measurement thereof. However, the signal may also or alternatively be associated with another part of the body, e.g. a myocardial discharge, which nevertheless is indicative of an action causing flow, e.g. of a pulse wave.

Because the sensors are a known distance apart, recognition of the signals for e.g. a pressure wave (caused by deformation of the arterial wall as blood passes therealong) by the sensors can be calculated against the known distance to provide a velocity measurement. An acceleration measurement could also be provided. The system is non-invasive by relying on the detection of a bodily signal. Many electrical signals can relatively easily be detected. Mechanical signals can be based on the mechanical relation between skin movement and the sensors located thereon.

The sensors can be electrodes, or e.g. piezoelectric sensors adapted to convert mechanical stress or strain into proportionate electrical energy. One major benefit of piezoelectric film is its low acoustic impedance when close to human tissue. This therefore permits more efficient transduction of acoustic signals in tissue. Piezoelectric films also have a high degree of elastic resilience, and consequently a low mechanical quality factor (Q).

Other sensors include liquid strain gauges, such as conductive oils/gels and new forms of carbon loaded liquids and electrolyte (e.g. Na Cl) gauges, as well as conductive polymer wires.

Indium: Galium In/Ga is also a suitable strain gauge sensor for biomedical sensors because it is liquid at room temperature, safe, inexpensive and its sensor properties are within the required range for bio-fluid pulse monitoring. When In/Ga is inserted into a flexible polymer tube and metal electrodes are attached at either end, the resistive or conductive properties will vary with strain. In/Ga sensors have demonstrated that when applied to this fluid monitoring that they can provide excellent measurement properties, such as conformal attachment, fast response times, good resolution and suitable mechanical attributes.

Preferably, the mechanical sensors are polyvinylidene fluoride (PVDF) sensors. PVDF is resistant to most chemical substances and is not sensitive to radiation.

Different sensors would be suitable for different positions, signals, or parts of the body, depending on the degree of sensitivity required, signal-to-noise ratio, locational difficulties, etc. Preferably, the sensor means wholly or substantially conform to the body area on which they are located. The part of the sensor means interfacing with the body could be a flexible polymeric material.

The measuring method and system of the present invention may comprise any number of sensor means. In one embodiment of the present invention, the sensors may be wholly or substantially longitudinally aligned so as to be locatable along the path of the conduit such as an artery. In an alternative embodiment, a number of sensors may be strategically located across an area, possibly in rows, so as to be located across an area of the human or animal body. Measurements can be taken from those sensors providing the strongest signals, and therefore expectedly located above the path of e.g. the largest and strongest artery. Accurate location of the sensors or means to support the sensors may then be less essential.

The system of the present invention may also have one sensor means, being pressure or electrical such as an ECG electrode, located on another part of a subject to provide a timing start e.g. on the chest for arterial blood flow and/or a pulse wave, to a distal sensor means.

The system could also be combined with other medical appliances such as a blood pressure reading means.

The sensor means may be arranged along a support means. The support means may have any suitable shape, size and design such that it is locatable, fittable and preferably attachable on or around a part of a human or animal body. The support means may be integral with or separable from one or more of the sensor means. The support means may comprise one or more separable portions, each portion optionally having one or more sensor means therewith.

In one preferred embodiment of the present invention, the support means comprises a collar or a cuff adapted to be locatable around an elongate portion of a human or animal body such as an arm.

Also preferably, the support means includes means to attach or fit itself around or onto the human or animal body. The support means may include one or more fastening means such as VELCRO (RTM). The support means may also include means to adjust its fittment or attachment to the human or animal body such as an eternal or internal inflatable bag.

The support means may be wholly or substantially rigid, or be wholly or substantially flexible, whilst also possibly including a wholly or substantially rigid frame, or a rigid frame piece. The support means may include a reference means or portion, adapted to reference the support means to a part of the human or animal body, e.g. the thumb, wrist or elbow, to ensure that the sensors are wholly or substantially relocatable when repeat or comparative measurements are desired or necessary.

The support means may also comprise one or more parts adapted to conjoin the support means to the human or animal body, and one or more parts adapted to support the sensor means to allow their location and sensitive movement on the human or animal body.

In one preferred embodiment of the present invention, the support means comprises one or more pockets arranged in a wholly or substantially rigid frame, which pocket(s) support a sensor means to allow mechanical conjoining of the sensor means to the skin of the human or animal body.

Thus, according to a second aspect of the present invention, there is provided a support means for two or more sensor means for measuring the flow of a human or animal bodily action or fluid along or through a conduit, such as pulsed wave velocity, comprising a wholly or substantially rigid frame and a pocket means for each sensor, the pocket means adapted to support a sensor means and allow sensitive movement thereof.

The means to transfer signals from the measuring system or method of the present invention includes any suitable signal transfer means which can be directly or remotely connected to a signal processing means. The transfer signal means could simply be a wire lead for connecting into a signal processing means such as a computer or other analysing unit or means. The signal transfer means could also be adapted to transmit a signal to a separate or remote signal processing unit, either directly or via other telemetry means such as a telephone network.

According to a particular embodiment of the present invention, there is provided a method of measuring pulsed wave velocity comprising the steps of:

locating two or more pressure sensor means wholly or substantially along the path of a bodily fluid conduit of a human or animal body, measuring the signals from the sensors based on deformation of the conduit wall as fluid passes therethrough, and calculating pulse wave velocity from the timing of the signals and distance between the sensors.

Preferably, the pressure sensor means are piezoelectric sensors in a support means.

Embodiments of the present invention will now be described by way of example only and with reference to the accompanying diagrammatic drawings in which:

FIG. 1 is an arterial pressure wave form;

FIGS. 2a and b are perspective and end views respectively of a pulsed wave velocity measuring system according to one embodiment of the present invention;

FIG. 4b is a sensor mount for a sensor means useable for the present invention;

FIG. 4c is a sample In/Ga sensor arrangement;

Figure 8:

FIGS. 6a–d are graphs of pressure wave forms of Subjects 1–4 measured according to the present invention;

FIGS. 7a–d are bivariate scatterplots based on multiple regression of the pulsed wave velocity systolic pressure measurements from the graphs of FIGS. 6a–d; and FIG. 8 is a human ejaculation spectrum.

Following each cardiac contraction, fresh blood is pumped throughout the body. This generates a pressure wave in the aorta. Pulsed wave velocity is the velocity of the pulse pressure wave-form. It depends on the artery and the condition of the person.

The radial stress applied on the arterial wall by the pressure wave creates a local defamation which propagates from the heart to peripheral sites. The pulse pressure wave-form results from the ejection of blood from the left ventricle and moves with a velocity much greater (about 5 to 10 m/s) than the forward movement of the blood itself.

The definition equation is:

$$PWV = k \cdot \sqrt{[V \cdot \Delta P / \Delta V]}$$

[where: PWV: Pulse Wave Velocity; k: constant; V: Initial Vessel Volume; $\Delta P$: Pressure Delta; $\Delta V$: Vessel Volume Delta;]

With increased vessel wall stiffness (decreased compliance), $\Delta V$ decreases and pulse wave velocity increases. With increased blood pressure, the arterial walls are stretched more strongly and pulse wave velocity increases. Accordingly, for a fixed vessel distance, as the PWV increases the blood pressure increases as well.

As pressure waves travel form the aorta and large arteries to the narrower, less compliant distal arteries, they travel at a greater speed. A hardened artery will yield a higher PWV due to the reduced resistance exerted to the pulse wave, and the wave will be reflected with greater intensity.

Figure 1:
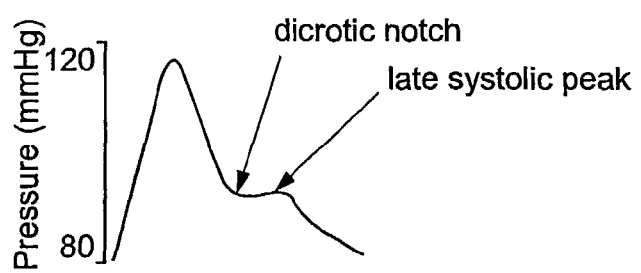

FIG. 1 shows a theoretical in vivo arterial pressure wave form over time. This sequence shows a pressure pulse passing an observation point on the arterial tree. The symptomatic anomalies of the trace are identified as the late systolic peak and the dicrotic notch. Wave reflections can be quantified as the ratio of the height of the late systolic peak to the total height of the arterial pulse wave. Travel time of a reflective wave can be calculated from the foot of the pressure wave to the foot of the late systolic peak.

Figure 2A:
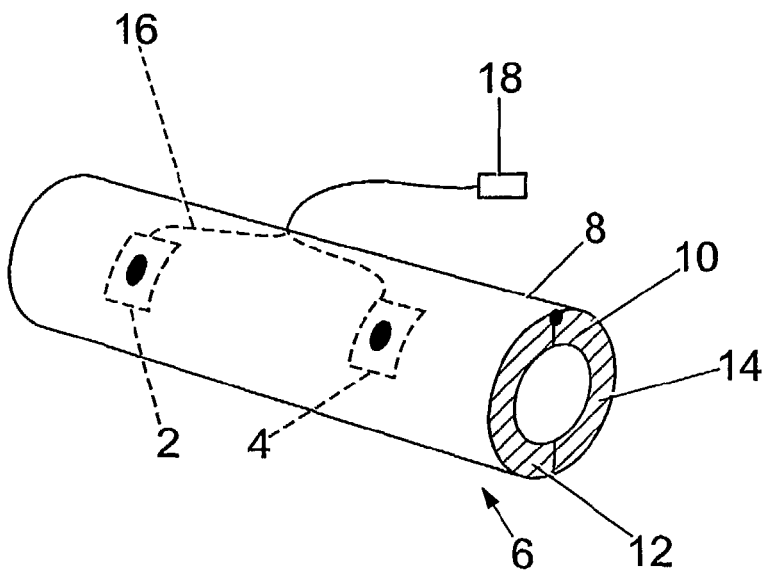
Figure 2B:
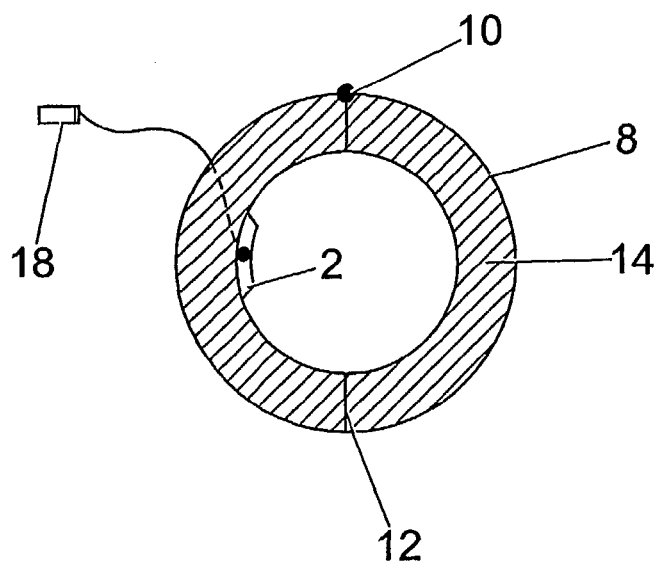

FIGS. 2a and b show a first pulse wave velocity measuring system according to the present invention. It comprises two sensor means 2, 4 located within a support means 6. The support means 6 comprises a wholly or substantially rigid tubular outer frame cuff 8, longitudinally hinged 10 and longitudinally separable opposite the hinge 12 (not shown).

Within the outer frame 8 the support means 6 has a coaxial flexible bag 14. The bag 14 is inflatable by any suitable means such as a hand pump. The sensors 2, 4 are located on the internal side of the bag 14. Leads 16 extend from each sensor 2, 4 into a single signal transfer means 18 which could be directly connectable into a signal processing means such as a computer or other analysis unit (not shown).

Figure 3:
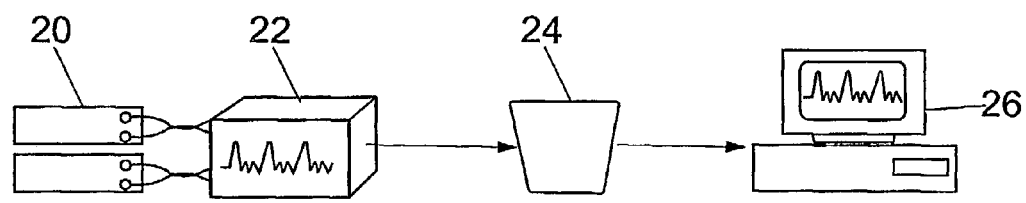
FIG. 3 is a schematic drawing of a human arm showing possible location of the measuring system of FIG. 2 along said arm.

FIG. 3 is a schematic drawing of two PVDF sensors 20 adapted to detect the pulse signal at two designated positions on a human or animal body. The sensors 20 are connected to an analogue processing circuit 22 to convert the charge generated by the sensors 20 into a voltage signal, to amplify the small signal, and to filter out any undesired frequencies. From there, the signal is transferred to a data acquisition board 24 to digitise the acquired signal, and then transferred to a computer 26 having relevant software to perform data logging, digital signal processing, computation of pulsed wave velocity, and analysis on the pressure wave profile.

Figure 4A:
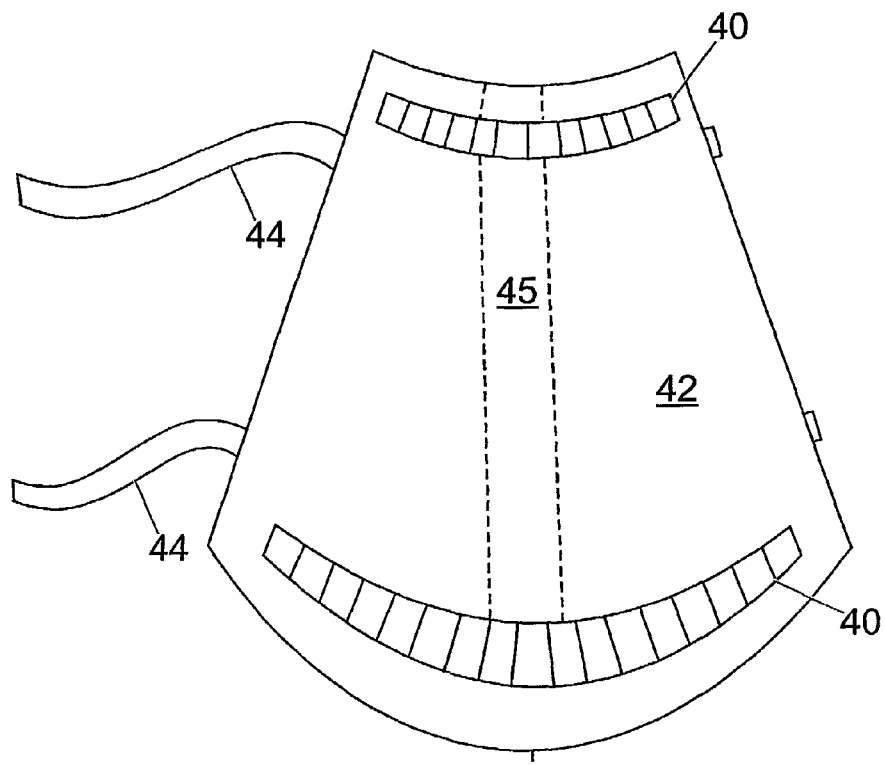
FIG. 4a is a pulse wave velocity measuring system according to a second embodiment of the present invention.
Figure 4A:
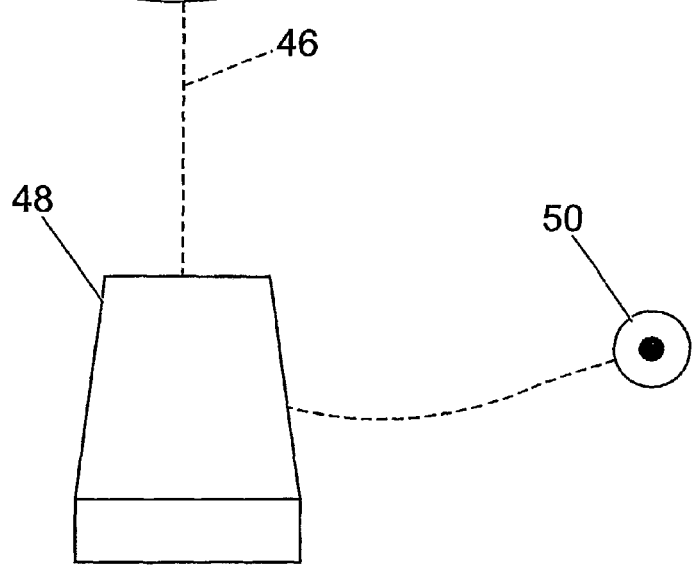
Figure 6A:
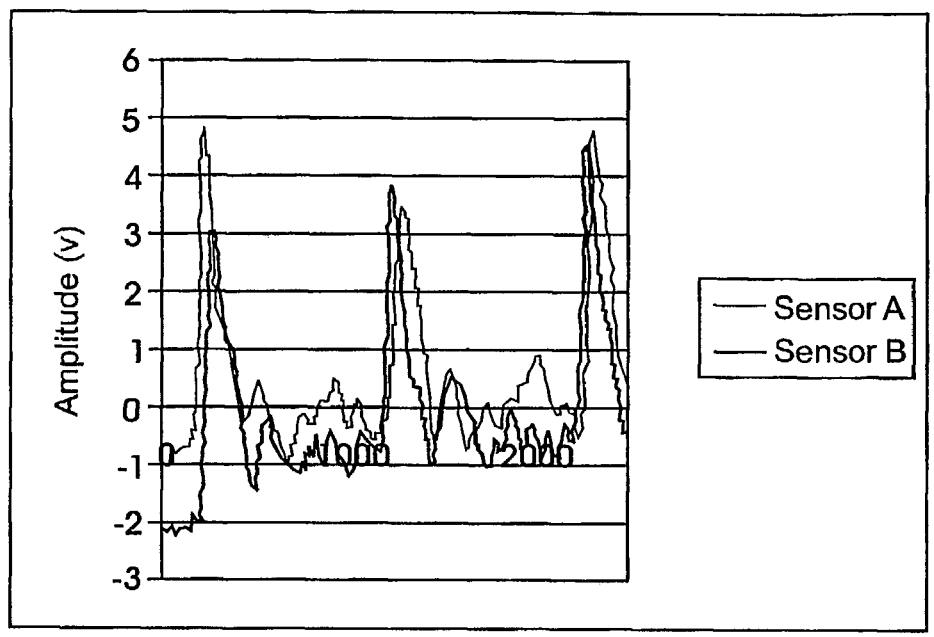
Figure 6B:
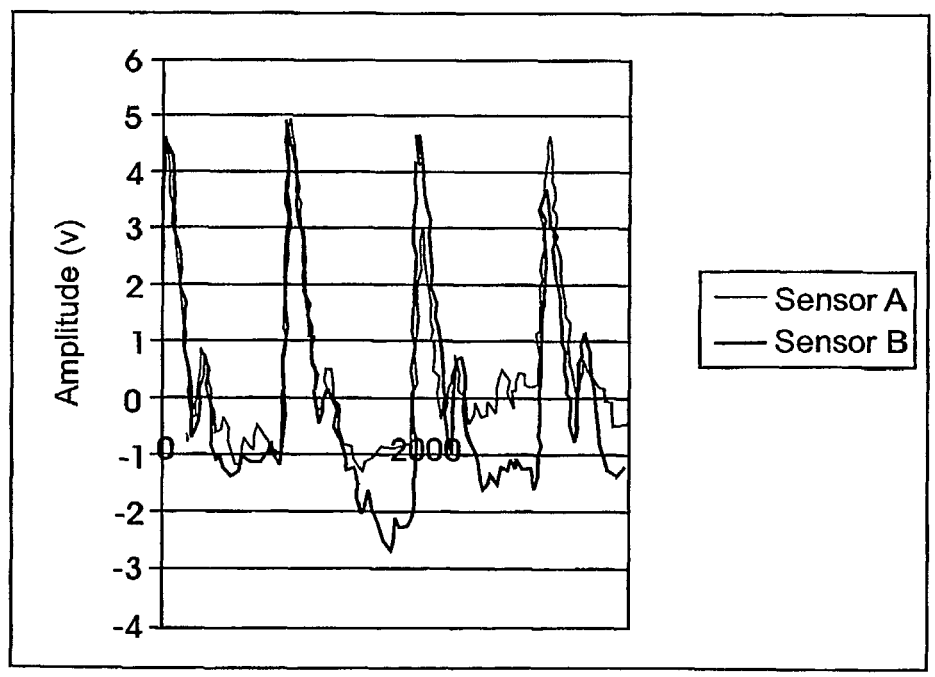
Figure 6C:
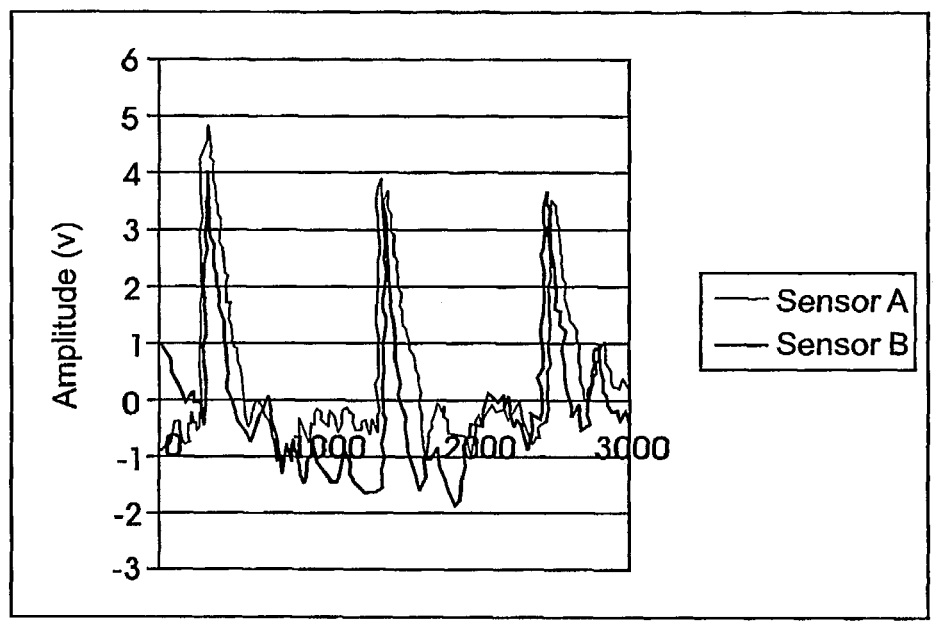
Figure 6D:
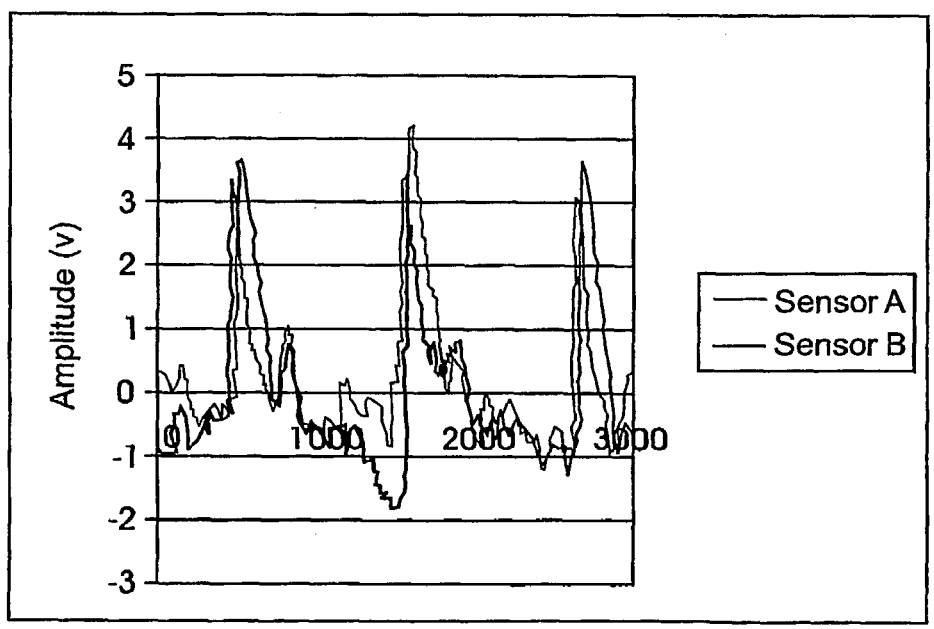
Figure 7A:
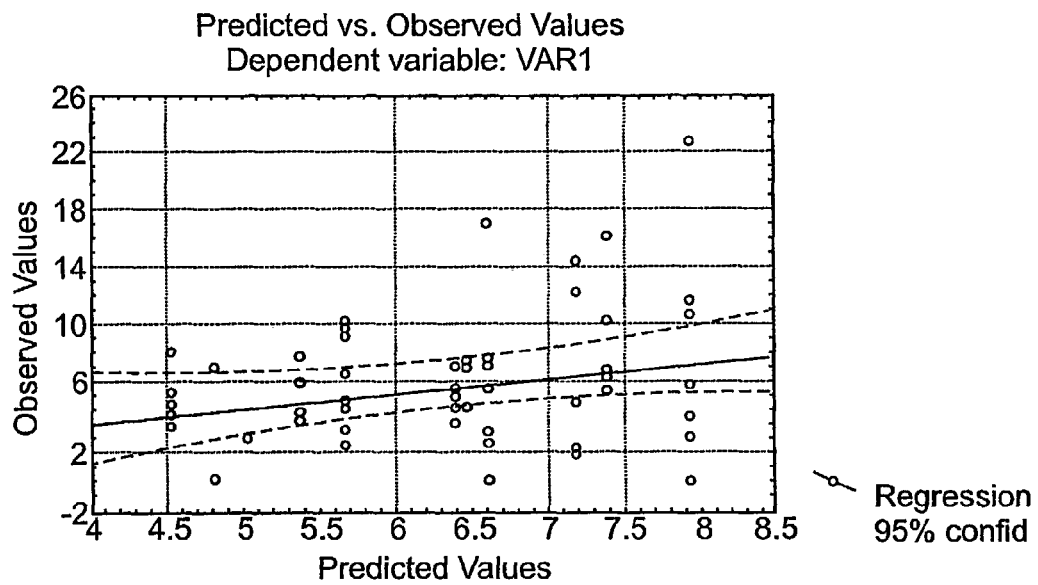
Figure 7B:
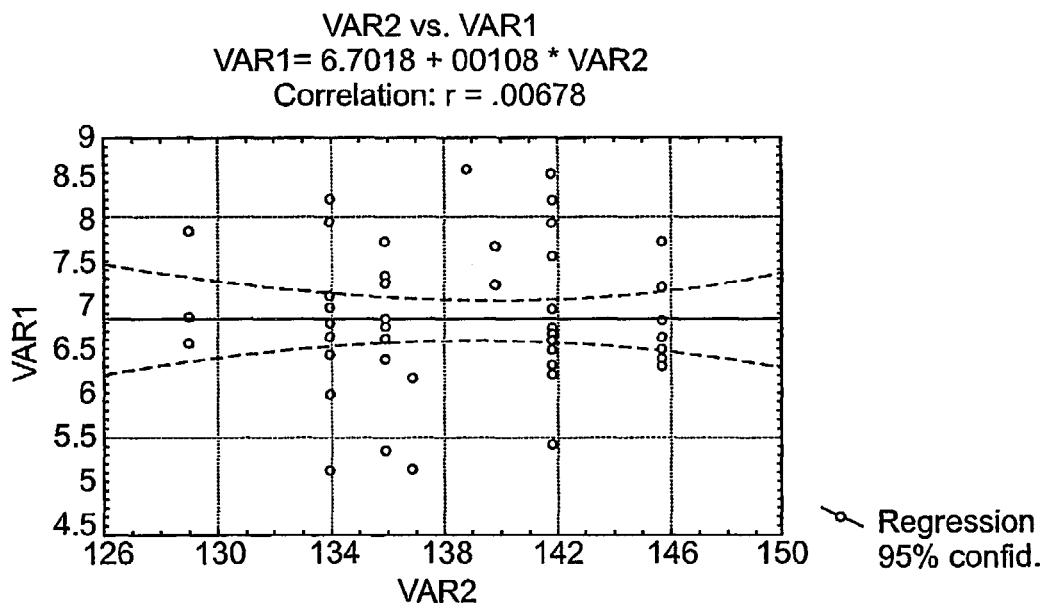
Figure 7C:
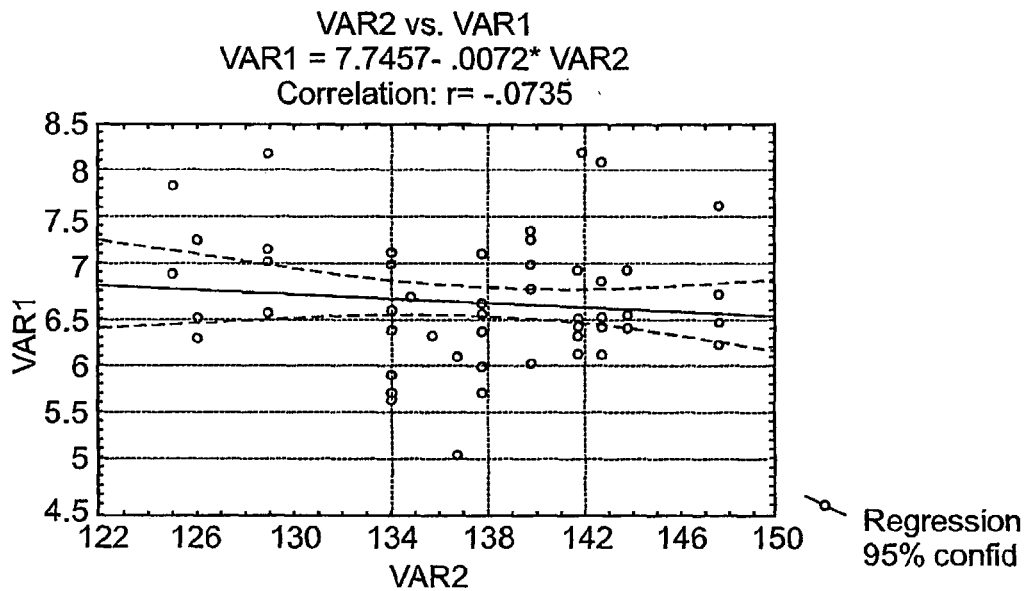
Figure 7D:
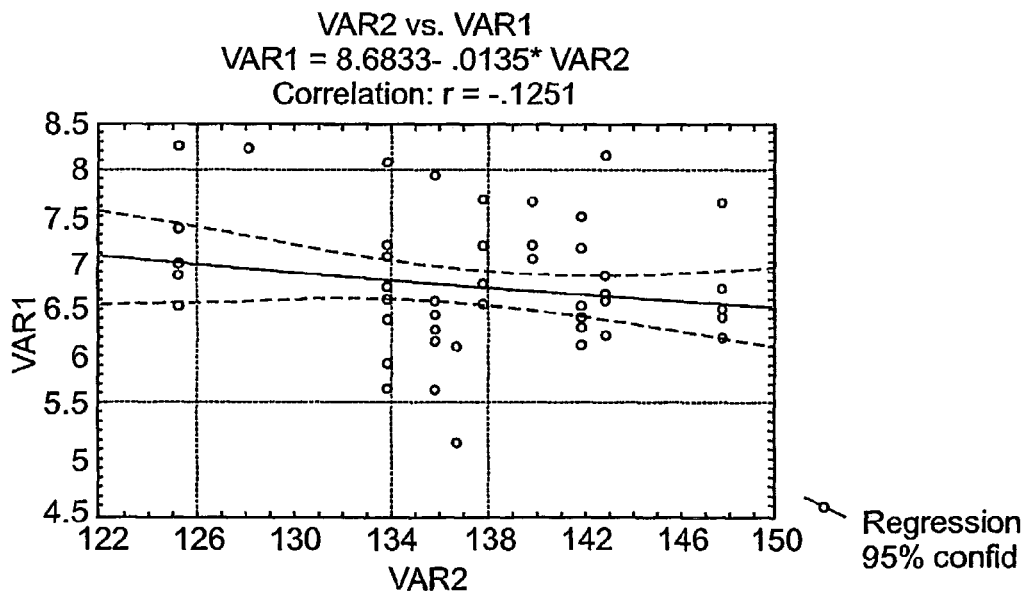

FIG. 4a shows a second pulse wave velocity measuring system. The system has two rows of sensor means 40 supported near the ends of an elongate flexible cuff 42. The cuff 42 can be located around the arm of a human subject (not shown), and fasteners 44 provide fixing of the cuff 42 around the arm.

The cuff 42 could include a rigid "spine" piece 45 (shown in dotted line) to assist comparative or reproducible locality of the cuff 42. That is, by ensuring that one end of the spine piece 45 always abuts the inner elbow between the upper and lower arms, it can be considered that the sensor means are located in the same general position for each measurement.

The sensors 40 are arranged so that at least one of the sensors 40 in each row will be located above an artery. The sensors 40 are connected by a lead 46 to a signal processing unit 48, which can analyse the signals from all the sensors and select the strongest or biggest signal from each row of sensors 40. Also connected to the processing unit 48 is an ECG electrode 50 attachable to the front of the chest of the subject, which can detect the initiation of the pulse wave at the heart, and so provide a timing or timed start of the pulse wave. This can be considered with the time taken for the pulse wave to get from the heart to the cuff sensors 40. The cuff pressure should be below the diastolic pressure.

FIG. 4b shows a sensor mount 52 for holding a PVDF sensor means 54. The mount 52 has an adjustable screw 56 acting on a plate 58, beneath which the sensor means 54 is locatable, with its edges held by clips 59 of the mount 52. Adjusting the screw 56 serves to adjust the height of the sensor means 54 relative to a conjoined cuff 60, and so optimise skin contact.

FIG. 4c shows a schematic view of the arrangement for an Indium/Galium sensor 60 having metal electrode heads 62, and an intermediate flexible tube 64 of Indium/Galium.

Figure 5:
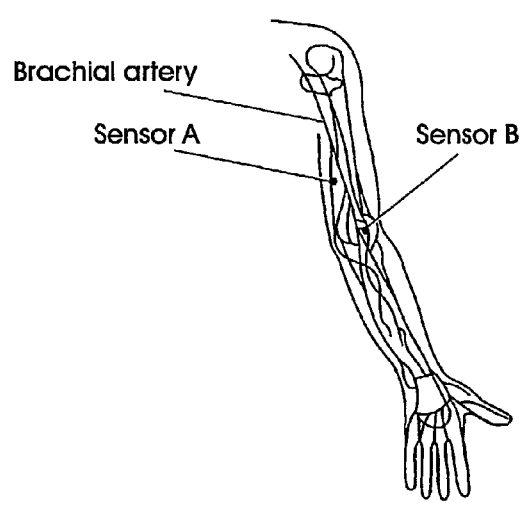
FIG. 5 is a schematic drawing of two pressure sensor means and associated signal processing means usable with the present invention.

FIG. 5 is a schematic drawing of a human arm on which the brachial artery is highlighted. For the experimental data hereinafter, a pulse wave velocity measuring system was located around subjects and the two sensors of said measuring system were located either as shown in FIG. 4a or FIG. 5.

In the experimental data hereinafter, Sensor A was an LTD series piezoelectric sensor generally having a protective coating piezo film and polyester laminate. Sensor B was a DT series of piezoelectric film element sensor having outer protective coatings, and a central piezo film sandwiched between metalization layers. Both these forms of sensors are PVDF sensors. The distance between the sensors was measured and recorded into the signal processing means.

Experimental Data

| Subject | Sex | Age | Fitness |
|---|---|---|---|
| 1 | Male | Mid 20's | Moderate |
| 2 | Male | Mid 20's | Athletic |
| 3 | Male | Mid 20's | Moderate |
| 4 | Male | Mid 20's | Athletic |

FIGS. 6a–d are graphs of pressure wave forms conducted on Subjects 1–4 respectively.

FIGS. 7a–d depict the findings of the linear regression of the unscreened PWV data of FIGS. 6a–d respectively. Those results which reside in the vacinity of the regression line in FIGS. 7a–d reflect the successful prediction of PWV values using the linear regression formula.

Analysis of this information also indicates that there is no linear relationship between PWV and systolic and diastolic pressures. The regression line being almost horizontal in FIGS. 7a–d also implies that there is no direct relationship between PWV and blood pressure. The table below summarises the results of the preliminary clinical trials regarding PWV and blood pressure (artificially increased via exercise).

| Subject | Strength of Systolic-PWV Relationship | PWV (m/s) Mean | PWV (m/s) Std. Dev |
|---|---|---|---|
| 1 | −0.0576 | 6.895 | 0.793 |
| 2 | 0.0001 | 6.851 | 0.767 |
| 3 | 0.0054 | 6.754 | 0.615 |
| 4 | −0.0157 | 6.819 | 0.650 |

The inference from these findings is that PWV remains consistent as blood pressure is increased through exercise.

The above data confirms that there was no significant relationship between PWV and blood pressure ("artificially" manipulated via exercise). PWV is a more reliable diagnostic tool in evaluating hypertension in a subject because blood pressure can be easily manipulated via exercise or indeed stress and can therefore often indicate erroneous values in the clinical assessment of a subject. PWV provides a more robust indicator in the clinical assessment of a subject.

Results here also indicated that PWV remains constant when a cuff is placed on the upper arm and remains inflated at sub-diastolic levels. However, once the cuff is inflated above the diastolic level, PWV will be greatly reduced and became more variant. This result is in agreement with traditional usage of cuff for blood measurement. As the cuff is inflated to occlude the artery, the pressure flow dynamics in the brachial artery becomes occluded when the cuff pressure exceeds the systolic level. As PWV is based on the detection of the blood pressure pulse, the turbulent dynamics caused by partial occlusion would account for the high variance in PWV above diastolic.

The obtained PWV values in the experiments were between 5.1 m/s and 11.2 m/s and the reproducibility varied between 9.11% and 11.50%. Although these values were not compared with an external reference system, the literature suggests PWV should be between 5 m/s and 15 m/s for subjects with similar age and health background. When analysing the data at the 5% confidence level, the percentage error of the mean was typically ≅3%, which suggests that the PWV data has a good central tendency. Again, this reflects the robust nature of PWV, and the reliability of the data acquired via this system.

FIG. 8 shows a profile of sperm load and events against time during ejaculation. The area under the graph is sperm load. The spectrum confirms the use of the present invention to provide a profile suitable for medical interpretation.

The present invention is a non-invasive way of measuring the flow of a bodily action or fluid along or through a conduit, such as pulse wave velocity. Pulse wave velocity in the brachial artery can provide an indication of vessel wall quality or stiffness, which in turn, can be used to indicate how an individual's vascular system is ageing. Disorders such as stenosis and complete occlusion can be diagnosed by accurate measurement of pulse wave velocity.

The present invention provides apparatus and method for simple and non-invasive measurement of the flow of a bodily action or fluid along or through a conduit of any patient or subject. Such data can easily be compared with 'normal' or 'typical' subject data for immediate analysis and diagnosis by a medical practitioner. Such data could also be relayed to a location using known telemetry should the subject be remote from the signal processing means.

What is claimed is:

1. A system of measuring the pulse wave velocity of a human or animal bodily action or fluid along or through a bodily flow conduit comprising two or more sensor means capable of substantially conforming to a body and detecting electrical signals, the sensor means located at least 2 centimeters apart on the body along or around the path of the conduit, a support means to apply a pressure below the diastolic pressure in the conduit wherein the sensor means are arranged in or on the support means, a signal processing means adapted to calculate the velocity between the sensor means, and means to transfer signals from the sensor means to the signal processing means.

2. A system as claimed in claim 1 wherein the bodily action is a pulse wave or pressure profile.

3. A system as claimed in claim 1 wherein the bodily fluid is blood, semen or urine.

4. A system as claimed in claim 1 wherein one or more of the sensor means measures a direct electrical and/or mechanical signal from the conduit.

5. A system as claimed in claim 1 wherein one or more of the sensor means measures an indirect electrical and/or mechanical signal from a conduit.

6. A system as claimed in claim 1 wherein one or more of the sensor means is selected from the group consisting of electrodes, liquid strain gauges, conductive polymer wires, mechanical sensors and Indium/Gallium sensors.

7. A system as claimed in claim 6 wherein the sensor means are piezoelectric sensors, polyvinylidine fluoride sensors or Indium/Gallium sensors.

8. A system as claimed in claim 1 wherein the sensor means wholly or substantially conform to the shape of the body on which they are located.

9. A system as claimed in claim 1 wherein the part of the sensor means interfacing with the body is a flexible polymeric material.

10. A system as claimed in claim 1 wherein the sensor means are wholly or substantially longitudinally aligned along the path of the conduit.

11. A system as claimed in claim 1 wherein the sensors are located in rows across an area of the human or animal body under which the conduit passes.

12. A system as claimed in claim 11, wherein the signal processing means analyzes the signals from the sensor means and selects at least one signal from each row of sensor means.

13. A system as claimed in claim 1 wherein the sensor means are integral with the support means.

14. A system as claimed in claim 1 wherein the sensor means are separable from the support means.

15. A system as claimed in claim 1 wherein the support means comprises a collar or a cuff adapted to be locatable onto or around an elongate portion of a human or animal body.

16. A system as claimed in claim 1 wherein the support means includes means to attach or fit itself onto or around the human or animal body.

17. A system as claimed in claim 1 wherein the support means includes a reference means or portion adapted to reference the support means to a part of the human or animal body.

18. A system as claimed in claim 1 wherein the support means comprises one or more pockets, which pocket supports a sensor means.

19. A system as claimed in claim 1 wherein one or more sensor means are additionally located at a distal location on the human or animal body.

20. A system as claimed in claim 19, wherein the bodily action is a pulse wave or pressure profile and wherein the one or more distally located sensor means detects an initiation of the pulse wave or pressure profile thereby providing a timed start of the pulse wave or pressure profile.

21. A system as claimed in claim 1 for measuring the pulse wave velocity along a human artery.

22. A system as claimed in claim 1 for measuring the velocity and/or volume of seminal fluid during ejaculation.

23. A system as claimed in claim 1 for measuring a pressure, volume or event-timing occurring along or through the conduit.

24. A method of measuring the flow of a human or animal bodily action or fluid along or through a bodily flow conduit, which method comprises using the system as claimed in claim 1.

25. A support means for two or more sensor means for measuring the flow of a human or animal bodily action or fluid along or through a conduit as described in claim 1, comprising a frame and a support for each sensor means adapted to allow sensitive movement thereof.

26. A support means as claimed in claim 25, wherein the frame is wholly or substantially rigid.

27. A system as claimed in claim 1, wherein the support means comprises
an adjustable fastener; and
a frame in communication with the adjustable fastener.

28. A method of measuring the pulse wave velocity of a human or animal bodily action or fluid along or through a bodily flow conduit, the method comprising the steps of:
  locating two or more sensor means at least 2 centimeters apart wholly or substantially along the path of the conduit of a human or animal body, the sensor means capable of substantially conforming to the body and detecting electrical signals, and locating support means on the body to apply a pressure below the diastolic pressure in the conduit;
  measuring the signals from the sensors based on deformation of the conduit wall as fluid passes therethrough; and
  calculating the pulse wave velocity from the timing of the signals and distance between the sensors.

29. A method as claimed in claim 28 wherein the sensor means are piezoelectric sensors in the support means.

30. A method as claimed in claim 28, wherein the sensor means are located in rows further comprising
  analyzing the signals from the sensor means; and
  selecting at least one signal from each row of sensor means.

31. A method as claimed in claim 28, wherein the bodily action is a pulse wave or pressure profile further comprising
  detecting an initiation of the pulse wave or pressure profile; and
  providing a timed start of the pulse wave or pressure profile.

* * * * *